United States Patent
Ebbrecht et al.

(10) Patent No.: US 6,552,092 B2
(45) Date of Patent: Apr. 22, 2003

(54) DEFOAMERS FOR AQUEOUS MEDIA

(75) Inventors: Thomas Ebbrecht, Bochum (DE); Michael Gippert, Essen (DE); Martina Hartmann, Duisburg (DE); Wolfgang Josten, Königswinter (DE); Peter Muss, Essen (DE); Stefan Silber, Krefeld (DE); Roland Sucker, Werne (DE)

(73) Assignee: Goldschmidt AG, Essen (DE)

( * ) Notice: Subject to any disclaimer, the term of this patent is extended or adjusted under 35 U.S.C. 154(b) by 0 days.

(21) Appl. No.: 10/068,522

(22) Filed: Feb. 5, 2002

(65) Prior Publication Data

US 2002/0169217 A1 Nov. 14, 2002

Related U.S. Application Data

(63) Continuation of application No. 09/548,513, filed on Apr. 13, 2000, now Pat. No. 6,420,324.

(30) Foreign Application Priority Data

Apr. 16, 1999 (DE) .......................... 199 17 186

(51) Int. Cl.⁷ .......................... B01F 3/12; B01D 19/04; C07C 275/06
(52) U.S. Cl. .......................... 516/31; 516/20; 516/123; 516/124; 516/131; 564/58; 564/59; 564/61; 564/73
(58) Field of Search ................. 516/130, 131, 516/123, 124, 53, 77; 564/58, 59, 61, 73; 508/552

(56) References Cited

U.S. PATENT DOCUMENTS

| | | | |
|---|---|---|---|
| 2,683,699 A | 7/1954 | Gehring | 524/213 |
| 2,710,840 A | 6/1955 | Swakon | 508/552 |
| 2,832,739 A | 4/1958 | Swakon | 508/552 |
| 3,211,692 A | 10/1965 | Hopkins et al. | 524/216 |
| 3,819,561 A | 6/1974 | Bruenner | 524/212 |
| 4,082,689 A | 4/1978 | Heyden et al. | 516/123 |
| 4,696,761 A | 9/1987 | Haubennestel et al. | 516/130 |
| 6,214,774 B1 * | 4/2001 | Nozaki et al. | 508/552 |
| 6,420,324 B1 * | 7/2002 | Ebbrecht et al. | 508/552 |

FOREIGN PATENT DOCUMENTS

EP 0 115 585 A1 8/1984

* cited by examiner

*Primary Examiner*—Daniel S. Metzmaier
(74) *Attorney, Agent, or Firm*—Frommer Lawerence & Haug LLP

(57) ABSTRACT

The invention relates to compositions for defoaming aqueous media, comprising as defoamers urea derivatives of the formula I

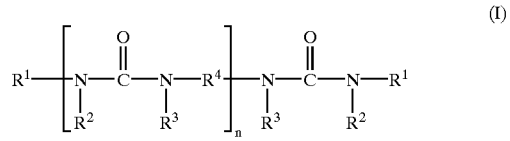

where $R^1$—is a hydrocarbon radical, preferably having 4 to 30 carbon atoms or a hydrocarbon radical, preferably having 4 to 24 carbon atoms and one nitrogen atom or a hydrocarbon radical, preferably having 4 to 30 carbon atoms and one carbonyl group, $R^2$—is a hydrogen atom or a hydrocarbon radical, preferably having 1 to 24 carbon atoms, $R^3$—is a hydrogen atom or a hydrocarbon radical, preferably having 1 to 24 carbon atoms, $R^4$—is an organic radical, preferably having 2 to 30 carbon atoms, and n—is from 0 to 5; in the form of solid particles, which are obtained by crystallization from a clear homogeneous melt dispersed in a carrier medium, and a process of preparation thereof.

3 Claims, No Drawings

DEFOAMERS FOR AQUEOUS MEDIA

RELATED APPLICATION

This application is a continuation of application U.S. Ser. No. 09/548,513, filed on Apr. 13, 2000 and now U.S. Pat. No. 6,420,324, which in turn claims priority to German Patent Application No. 199 171 86.6, filed Apr. 16, 1999, herein incorporated by reference.

BACKGROUND OF THE INVENTION

1. Field of the Invention

The invention relates to defoamers for aqueous media, comprising as hydrophobic solids critically influencing the defoaming certain urea derivatives which acquire the properties requisite for their particular activity as defoamers by crystallization from a clear melt dispersed homogeneously in the carrier medium.

2. Related Art

In many industrial processes, and especially when working in aqueous media, it is necessary to suppress, or prevent entirely, the unwanted formation of foam during the preparation or processing operations. This can be achieved by adding what are known as antifoams or defoamers, which even when used at very low concentrations upward of about 0.001% by weight are able to prevent or destroy unwanted foams. Examples of such prior art defoamers are silicone oils, mineral oils, hydrophobic polyoxyalkylenes, long-chain alcohols, and also mixtures of these products with one another and emulsions thereof. To reinforce the activity, it is common to add hydrophobic solids in amounts of from 0.1 to 10% by weight, which specifically promote dewetting processes on foam lamellae and therefore very actively assist in foam collapse. Suitable hydrophobic solids are appropriate silicas, metal stearates, polyolefins, and waxes.

The use of urea and urea derivatives as additives to defoamer formulation is also known per se.

European Patent No. EP-A-0 115 585, which corresponds to U.S. Pat. No. 4,696,761, describe ureas which are prepared in situ in an organic carrier medium at relatively low temperatures and which have defoaming properties for aqueous media. They are obtained by combining preferably equivalent amounts of isocyanates and amines in the organic carrier medium in question at temperatures below the melting point of the reaction product.

This gives urea derivatives of the general formula

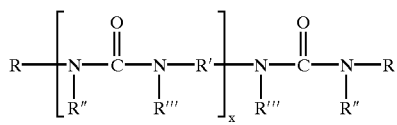

R=alkyl $C_4$–$C_{30}$
R'=single chemical bond; alkylene $C_2$–$C_{12}$, mono- to dinuclear aryl radicals which have additional alkyl groups $C_1$–$C_9$ on the aryl radical; cycloalkylene
R''=H, alkyl $C_1$–$C_{24}$
R'''=H, —$CH_3$
x=0.5.

It is expressly emphasized that when heated beyond their melting point, or when prepared at above their melting point, the ureas possess only an insignificant defoaming action. This is correlated with the formation of monodisperse or micellar structures during the in situ formation of the urea derivatives.

A disadvantage here is that, as a result of the in situ formation of the urea derivatives in accordance with the procedure described in EP-A-0 115 585, it is necessary to resort to carrier media which cannot react with amines and in particular not with isocyanates either. For example, the hydroxy-functional polyoxypropylenes well-known to the skilled worker as carrier media for defoamers, and hydroxy-functional polyoxyalkylene-polysiloxanes as well, are rejected on account of their hydroxyl functionality. It is true that, in principle, the reaction of an amine with an isocyanate is clearly preferred over the reaction of a hydroxy compound with an isocyanate, in respect of the reaction rate; however, and especially in the presence of the amines, which are known to be catalysts for the nucleophilic addition of hydroxy compounds onto isocyanates, hydroxy compounds react as well to uncontrollable extents and so result in urea derivatives which it is difficult, if possible at all, to crystallize. This would of course directly affect the activity of the resulting urea derivatives and would result at least in results that are difficult if not impossible to reproduce in the context of their use as defoamers.

BRIEF SUMMARY OF THE INVENTION

This invention provides a composition for defoaming aqueous media, comprising as defoamers urea derivatives of the formula I

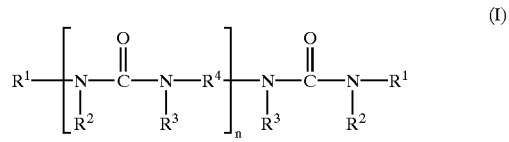

where
$R^1$—is a hydrocarbon radical or a hydrocarbon radical and one nitrogen atom or a hydrocarbon radical and one carbonyl group,
$R^2$—is a hydrogen atom or a hydrocarbon radical,
$R^3$—is a hydrogen atom or a hydrocarbon radical,
$R^4$—is an organic radical, and
n—is from 0 to 5; in the form of solid particles, which are obtained by crystallization from a clear homogeneous melt dispersed in a carrier medium.

This invention also provides a process for preparing a solid particle urea derivative of the formula I

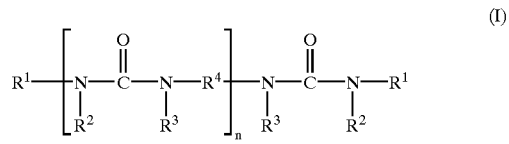

where
$R^1$—is a hydrocarbon radical or a hydrocarbon radical having one nitrogen atom or a hydrocarbon radical having one carbonyl group,
$R^2$—is a hydrogen atom or a hydrocarbon radical,
$R^3$—is a hydrogen atom or a hydrocarbon radical,
$R^4$—is an organic radical, and
n—is from 0 to 5;
comprising the steps of
  (a) heating the urea derivative solution in a first carrier media above the melting points of said urea derivative to form a homogeneous solution and (b) mixing the homogeneous solution of step (a) with a second carrier media having a temperature of less than 25° C.

DETAILED DESCRIPTION OF THE INVENTION

It has surprisingly now been found that, for the preparation of defoamer formulations containing urea derivatives as hydrophobic solids, the above-described in situ preparation of such urea derivatives below their melting point is neither necessary nor advantageous and that, instead, by means of controlled melting and recrystallization processes, it is possible to prepare defoamer formulations having improved properties and which, indeed, through the methodical variation of melting and recrystallization conditions, permit custom-tailored property profiles. By preparing the urea derivatives separately it is also possible, if required, to use exclusively carrier media which on account of their potential reactivity with respect to amines and/or isocyanates, because of the side reactions described above, are not amenable to precipitative crystallization in the manner described in EP-A-0 115 585. These include, for example, hydrophobic polyoxyalkylenes and organomodified siloxanes, which may also contain hydroxy functions.

This procedure is specifically successful even with urea derivatives which are explicitly described in EP-A-0 115 585 and which therefore, in accordance with the prior art, in the case of the process described in this patent, should no longer show any extraordinary activity in defoamer formulations. Such urea derivatives are easy to prepare from the corresponding isocyanates and amines.

The invention therefore provides compositions for defoaming aqueous media, comprising as defoamers urea derivatives of the formula I

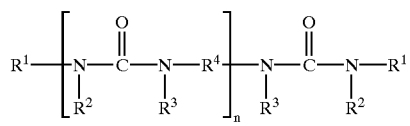

where

R$^1$—is a hydrocarbon radical, preferably having 4 to 30 carbon atoms, or a hydrocarbon radical, preferably having 4 to 24 carbon atoms, and one nitrogen atom or a hydrocarbon radical, preferably having 4 to 30 carbon atoms and one carbonyl group, R$^2$—is a hydrogen atom or a hydrocarbon radical, preferably having 1 to 24 carbon atoms, R$^3$—is a hydrogen atom or a hydrocarbon radical, preferably having 1 to 24 carbon atoms, R$^4$—is an organic radical, preferably having 2 to 30 carbon atoms, and n—is from 0 to 5; in the form of solid particles, which are obtained by crystallization from a clear homogeneous melt dispersed in a carrier medium.

Preferred compositions are those in which R$^1$ is a hydrocarbon radical having 4 to 24 carbon atoms, R$^2$ is a hydrogen atom, R$^3$ is a hydrogen atom, and R$^4$ is a hydrocarbon radical having 2 to 24 carbon atoms.

Preference is further given to those compositions of the invention in which R$^1$ is the organic radical

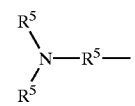

where R$^5$ is a hydrocarbon radical having 1 to 18 carbon atoms, R$^2$ and R$^3$ are a hydrogen atom, and R$^4$ is a hydrocarbon radical having 2 to 24 carbon atoms.

In addition, those compositions of the invention comprising as defoamers urea derivatives in which R$^1$ is the organic radical

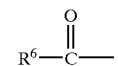

where R$^6$ is an organic radical having 2 to 30 carbon atoms, R$^2$ and R$^3$ are a hydrogen atom, and R$^4$ is a hydrocarbon radical having 2 to 24 carbon atoms, and compositions comprising as defoamers urea derivatives in which R$^1$ is a hydrocarbon radical having 2 to 24 carbon atoms, R$^2$ and R$^3$ are a hydrogen atom, and R$^4$ is the organic radical

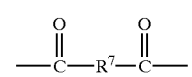

where R$^7$ is a hydrocarbon radical having 2 to 20 carbon atoms, are preferred compositions according to the present invention.

This invention also provides a cooling lubricant, a polymer dispersion, a coating material or a printing ink, comprising compositions for defoaming aqueous media wherein the compositions further comprise as defoamers urea derivatives of the formula I

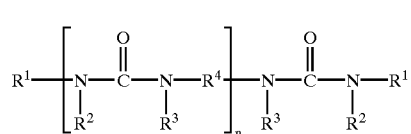

where

R$^1$—is a hydrocarbon radical, preferably having 4 to 30 carbon atoms, or a hydrocarbon radical, preferably having 4 to 24 carbon atoms, and one nitrogen atom or a hydrocarbon radical, preferably having 4 to 30 carbon atoms, and one carbonyl group, R$^2$—is a hydrogen atom or a hydrocarbon radical, preferably having 1 to 24 carbon atoms, R$^3$—is a hydrogen atom or a hydrocarbon radical, preferably having 1 to 24 carbon atoms, R$^4$—is an organic radical, preferably having 2 to 30 carbon atoms, and n—is from 0 to 5;

in the form of solid particles, which are obtained by crystallization from a clear homogeneous melt dispersed in a carrier medium.

This invention further provides a process for preparing a solid particle urea derivative of the formula I

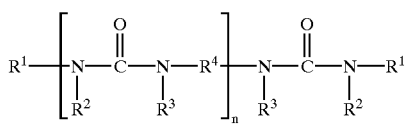

(I)

where
- $R^1$—is a hydrocarbon radical, preferably having 4 to 30 carbon atoms, or a hydrocarbon radical, preferably having 4 to 24 carbon atoms and one nitrogen atom, or a hydrocarbon radical, preferably having 4 to 30 carbon atoms and one carbonyl group,
- $R^2$—is a hydrogen atom or a hydrocarbon radical, preferably having 1 to 24 carbon atoms,
- $R^3$—is a hydrogen atom or a hydrocarbon radical, preferably having 1 to 24 carbon atoms,
- $R^4$—is an organic radical, preferably having 2 to 30 carbon atoms, and
- n—is from 0 to 5 which
comprising the steps of
   (a) heating the urea derivative solution in a first carrier media above the melting points of said urea derivative to form a homogeneous solution and
   (b) mixing the homogeneous solution of step (a) with a second carrier media having a temperature of less than 25° C.

For the present invention, therefore, it is completely irrelevant whether the urea derivatives of the invention are prepared separately and introduced as solids or are generated in the form of a precipitative crystallization in a liquid phase. An important feature at this point, in contrast, are the melting and recrystallization processes, which for the easy-to-prepare urea derivatives described herein result in surprising properties as hydrophobic solids in defoamers.

To this end, the recrystallization of the melted urea derivatives must take place from a clear melt dispersed homogeneously in the carrier medium, in order to reach optimum activity. This is easily possible by varying the main parameters, such as the chemical nature of the carrier oil, the urea derivative, and the temperature.

If the urea derivatives are merely melted in the carrier medium to form a non-homogenous mixture, i.e. not a clear mixture, the process of the invention cannot be used to prepare defoamers having sufficient activity.

The practical implementation of the above-described melting and recrystallization processes can be carried out by various methods. For example, the crystallization of the urea derivative melted in a carrier medium A can be influenced within a wide range, depending on the choice of the temperature gradients and the nature and extent of the shear energy employed, by addition of or addition to a carrier medium B of defined temperature. In this context, carrier media A and B can be identical or different.

Likewise, the melts of the urea derivatives can also be induced to crystallize in a particular way by measures ranging from simply leaving them to stand at room temperature through to the supply of external cooling by means of coolants. Here again, the chosen circumstances define the crystallization form of the urea derivatives and thus the activity of the resultant defoamer formulations. For instance, the recrystallization of the melted urea derivatives can also be carried out with advantage in the presence of additional solids, which can serve as crystallization nuclei, in order to obtain particular desired crystal morphologies.

In order to obtain urea derivatives which are as effective as possible in terms of the present invention, it is important to form particularly small, spherical urea crystals. This can be specifically influenced by varying, for example, the concentration of the urea derivatives in the melt. The smaller the chosen concentration of the urea derivatives in the melt, the smaller the crystals that can be produced. Furthermore, the formation of small urea derivative crystals is favored by a large, rapidly traversed temperature gradient, when, for example, a hot melt is shock-cooled by pouring it into a much colder carrier medium. High stirring outputs with stirrers which ensure effective, thorough mixing prevent the development at this point of undesirably large, persistent concentration gradients, which in turn lead to relatively large crystals and/or agglomerates thereof. It is, however, also possible with advantage initially to establish, at least partially, conditions which ought to promote the formation of relatively small crystals and then to follow these by conditions which promote large crystals. For example, a melt can be cooled rapidly at first and then slowly thereafter. In this way it is ensured that there are numerous crystallization nuclei, formed suddenly, on which, subsequently and more slowly, regularly formed crystals grow.

Suitable carrier media include not only organic or mineral oils but also siloxanes or organomodified siloxanes.

Defoamers of this kind can also be converted into aqueous emulsions by adding emulsifiers.

The defoamers of the invention can be used, for example, to defoam cooling lubricants, polymer dispersions, coating materials, and printing inks.

EXAMPLES

Example 1

475 g of a naphthene-base mineral oil (40 mPas/25° C.) were charged at room temperature to a vessel having a stirrer apparatus, 14.36 g of benzylamine were added, and the mixture was stirred for 5 minutes. Following the addition of 10.64 g of hexamethylene diisocyanate with stirring, the sudden formation of a colorless precipitate was observed. The subsequent reaction period was 60 minutes.

Example 2

475 g of a polyethersiloxane (400 mPas/25° C.; refractive index n=1.440/25° C.; insoluble in water) were charged at room temperature to a vessel having a stirrer apparatus, 14.36 g of benzylamine were added, and the mixture was stirred for 5 minutes. Following the addition of 10.64 g of hexamethylene diisocyanate with stirring, the sudden formation of a colorless precipitate was observed. The subsequent reaction period was 60 minutes.

Example 3

475 g of a naphthene-base mineral oil (40 mPas/25° C.) were charged at room temperature to a vessel having a stirrer apparatus, 2.78 g of diaminopropane were added, and the mixture was stirred for 5 minutes. Following the addition of 22.22 g of octadecyl isocyanate with stirring, the sudden formation of a colorless precipitate was observed. The subsequent reaction period was 60 minutes.

Example 4

475 g of a polyethersiloxane (400 mPas/25° C.; refractive index n=1.440/25° C.; insoluble in water) were charged at room temperature to a vessel having a stirrer apparatus, 2.78 g of diaminopropane were added, and the mixture was stirred for 5 minutes. Following the addition of 22.22 g of octadecyl isocyanate with stirring, the sudden formation of a colorless precipitate was observed. The subsequent reaction period was 60 minutes.

Example 5 (Inventive)

250 g of the mixture prepared in Example 1 were heated to 170° C., forming a clear, homogeneous mixture. This hot mixture was then introduced into 250 g of cold, naphthene-base mineral oil (40 mPas/25° C.) and stirred up with it. Instantaneously, the formation of a finely dispersed, colorless precipitate and a sudden increase in the viscosity were observed.

Example 6 (Inventive)

250 g of the mixture prepared in Example 2 were heated to 170° C., forming a clear, homogeneous mixture. This hot mixture was then introduced into 250 g of cold polyethersiloxane (400 mPas/25° C.; refractive index n=1.440/25° C.; insoluble in water) and stirred up with it. Instantaneously, the formation of a finely dispersed, colorless precipitate and a sudden increase in the viscosity were observed.

Example 7 (Inventive)

250 g of the mixture prepared in Example 3 were heated to 170° C., forming a clear, homogeneous mixture. This hot mixture was then introduced into 250 g of cold, naphthene-base mineral oil (40 mPas/25° C.) and stirred up with it. Instantaneously, the formation of a finely dispersed, colorless precipitate and a sudden increase in the viscosity were observed.

Example 8 (Inventive)

250 g of the mixture prepared in Example 4 were heated to 170° C., forming a clear, homogeneous mixture. This hot mixture was then introduced into 250 g of cold polyethersiloxane (400 mPas/25° C.; refractive index n=1.440/25° C.; insoluble in water) and stirred up with it. Instantaneously, the formation of a finely dispersed, colorless precipitate and a sudden increase in the viscosity were observed.

Example 9 (Inventive)

225 g of naphthene-base mineral oil (40 mPas/25° C.) were mixed with 25 g of N',N''-propane-1,3-diylbis(N'-octadecylurea) and the mixture was heated to 170° C., forming a clear, homogeneous mixture. This hot mixture was then introduced into 250 g of cold, naphthene-base mineral oil (40 mPas/25° C.) and stirred up with it. Instantaneously, the formation of a finely dispersed, colorless precipitate and a sudden increase in the viscosity were observed.

Example 10 (Inventive)

250 g of the mixture prepared in Example 1 were heated to 170° C., forming a clear, homogeneous mixture. This hot mixture was then introduced into a mixture of 225 g of cold, naphthene-base mineral oil (40 mPas/25° C.) and 25 g of sorbitan trioleate-20 EO and stirred up with it. Instantaneously, the formation of a finely dispersed, colorless precipitate and a sudden increase in the viscosity were observed.

Example 11 (Inventive)

250 g of the mixture prepared in Example 2 were heated to 170° C., forming a clear, homogeneous mixture. This hot mixture was then introduced into a mixture of 225 g of cold polyethersiloxane (400 mPas/25° C.; refractive index n=1.440/25° C.; insoluble in water) and 25 g of sorbitan trioleate-20 EO and stirred up with it. Instantaneously, the formation of a finely dispersed, colorless precipitate and a sudden increase in the viscosity were observed.

Example 12 (Not Inventive)

250 g of the mixture prepared in Example 1 were stirred up with 250 g of naphthene-base mineral oil (40 mPas/25° C.).

Example 13 (Not Inventive)

250 g of the mixture prepared in Example 2 were stirred up with 250 g of polyethersiloxane (400 mPas/25° C.; refractive index n=1.440/25° C.; insoluble in water).

Example 14 (Not Inventive)

250 g of the mixture prepared in Example 3 were stirred up with 250 g of naphthene-base mineral oil (40 mPas/25° C.).

Example 15 (Not Inventive)

250 g of the mixture prepared in Example 4 were stirred up with 250 g of polyethersiloxane (400 mPas/25° C.; refractive index n=1.440/25° C.; insoluble in water).

Example 16 (Not Inventive)

250 g of the mixture prepared in Example 1 were stirred up with a mixture of 225 g of naphthene-base mineral oil (40 mPas/25° C.) and 25 g of sorbitan trioleate-20 EO.

Example 17 (Not Inventive)

250 g of the mixture prepared in Example 2 were stirred up with 225 g of polyethersiloxane (400 mPas/25° C.; refractive index n=1.440/25° C.; insoluble in water) and 25 g of sorbitan trioleate-20 EO.

Example 18 (Not Inventive)

In a stirred vessel, 130 g of a naphthene-base mineral oil (40 mPas/25° C.) were heated to 170° C., 1.82 g of octylamine were added, and the mixture was stirred until the amine has completely dissolved. Following the addition of 1.18 g of 1,6-hexamethylene diisocyanate and a subsequent reaction period of 30 minutes, the unclear, nonhomogeneous reaction mixture was introduced dropwise into 143 g of naphthene-base mineral oil (40 mPas/25° C.), cooled to 20° C., in a second stirred vessel, with thorough stirring and cooling. Instantaneously, the formation of a lumpy, flocculated, colorless precipitate was observed.

Example 19 (Not Inventive)

In a stirred vessel, 130 g of a naphthene-base mineral oil (40 mPas/25° C.) were heated to 190° C., 1.82 g of octylamine were added, and the mixture was stirred until the amine has completely dissolved. Following the addition of 1.18 g of 1,6-hexamethylene diisocyanate and a subsequent reaction period of 30 minutes, the unclear, nonhomogeneous reaction mixture was introduced driopwise into 143 g of naphthene-base mineral oil (40 mPas/25° C.), cooled to 20° C., in a second stirred vessel, with thorough stirring and cooling. Instantaneously, the formation of a lumpy, flocculated, colorless precipitate was observed.

Use Examples

The testing of the performance properties took place in a commercial cooling lubricant concentrate containing mineral oil, and two commercially available polymer dispersions.

Testing of the Defoaming Action in a Commercially Available Cooling Lubricant Concentrate 99.6 g of a commercial cooling lubricant concentrate containing mineral oil were admixed with 0.4 g of the defoamers prepared in accordance with Examples 5 to 9 and Examples 12 to 15, 18 and 19. 15 g of these mixtures were placed in a graduated 1000 ml measuring cylinder and made up to 300 ml with deionized water. This solution was then gassed using a D1 frit with an air speed of 1.8 l/minute. A measurement was made of the time, in seconds, required for the formation of 700 ml of foam.

TABLE 1

Results of performance testing in a cooling lubricant concentrate

| Added defoamer | Time to form 700 ml of foam |
| --- | --- |
| None | 22 seconds |
| Example 5 (inventive) | 2100 seconds |
| Example 6 (inventive) | 5220 seconds |
| Example 7 (inventive) | 1560 seconds |
| Example 8 (inventive) | 3840 seconds |
| Example 9 (inventive) | 1980 seconds |
| Example 12 (not inventive) | 480 seconds |
| Example 13 (not inventive) | 780 seconds |
| Example 14 (not inventive) | 180 seconds |
| Example 15 (not inventive) | 360 seconds |
| Example 18 (not inventive) | 110 seconds |
| Example 19 (not inventive) | 90 seconds |

As was evident from the examples shown, the inventive examples (Examples 5 to 9) were markedly superior to the noninventive examples (Examples 12 to 15, 18 and 19) in terms of their defoaming action. It was clear in particular that in order to obtain optimum activity from the defoamer formulations it was necessary for recrystallization of melted urea derivatives to take place from a clear melt dispersed homogeneously in the carrier medium.

Testing of the Defoaming Action in Commercially Available Polymer Dispersions

Testing was carried out in the styrene-acrylate dispersion Acronal® 290 D from BASF and in the all-acrylate dispersion Acronal® A603 from BASF.

The inventive and noninventive defoamers were each incorporated into the dispersions for one minute at 1000 rpm.

Air was introduced into the polymer dispersions containing defoamer additive using a turbine stirrer (diameter 4 cm) at 2500 rpm for 1 minute. Straight after switching off the stirrer, the aerated dispersion was placed in a measuring cylinder up to the 50 ml mark, and weighed. The weight was influenced by the amount of air introduced with stirring and was a measure of the activity of the defoamer.

TABLE 2

Results of performance testing in the polymer dispersion Acronal® 290 D

| Defoamer | Amount of defoamer in % by weight | Sample density in g/50 ml |
| --- | --- | --- |
| None | — | 39.3 |
| Example 10 | 0.2 | 49.6 |
| (inventive) | | |
| Example 11 | 0.05 | 50.0 |
| (inventive) | | |
| Example 16 | 0.2 | 43.6 |
| (not inventive) | | |
| Example 17 | 0.05 | 44.1 |
| (not inventive) | | |

TABLE 3

Results of performance testing in the polymer dispersion Acronal® A603

| Defoamer | Amount of defoamer in % by weight | Sample density in g/50 ml |
| --- | --- | --- |
| None | — | 38.1 |
| Example 10 | 0.2 | 48.8 |
| (inventive) | | |
| Example 11 | 0.05 | 49.2 |
| (inventive) | | |
| Example 16 | 0.2 | 42.5 |
| (not inventive) | | |
| Example 17 | 0.05 | 43.9 |
| (not inventive) | | |

As is evident from the examples shown, the inventive examples (Examples 10 and 11) are markedly superior to the noninventive examples (Examples 16 and 17) in terms of their defoaming action.

The above description is intended to be illustrative and not limiting. Various changes and modifications in the embodiments described herein may occur to those skilled in the art. Those changes can be made without departing from the scope or spirit of the invention.

What is claimed:

1. A urea derivative in the form of solid particles of the formula I

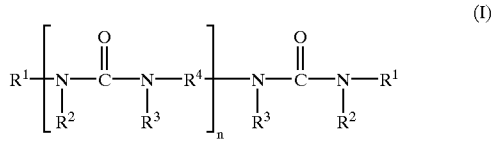

(I)

where $R^1$—is a hydrocarbon radical having 4 to 30 carbon atoms or a hydrocarbon, a hydrocarbon radical having 4 to 30 carbon atoms and one carbonyl group, or an organic radical of the formula:

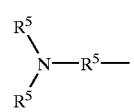

(II)

where $R^5$ is a hydrocarbon radical having 1 to 18 carbon atoms, $R^2$—is a hydrocarbon radical, $R^3$—is a hydrogen atom or a hydrocarbon radical, R[4]—is an organic radical, and n—is from 0 to 5.

2. A urea derivative in the form of solid particles of the formula I

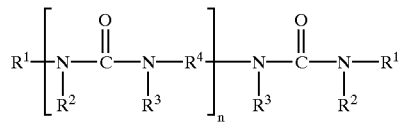
(I)

where is an organic radical of the formula:

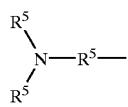
(II)

where R[5] is a hydrocarbon radical having 1 to 18 carbon atoms,

R[2]—is a hydrogen atom or a hydrocarbon radical,

R[3]—is a hydrogen atom or a hydrocarbon radical,

R[4]—is an organic radical, and n—is from 0 to 5.

3. A process for preparing a dispersion of urea derivatives in the form of solid particle of the formula I

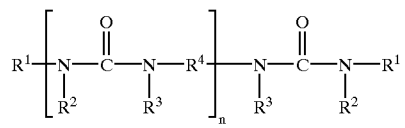
(I)

where

R[1]—is a hydrocarbon radical, a hydrocarbon radical having one nitrogen atom, or a hydrocarbon radical having one carbonyl group, R[2]—hydrogen hydrocarbon radical, R[3]—is a hydrogen atom or a hydrocarbon radical, R[4]—is an organic radical, and n—is from 0 to 5;

in carrier medium comprising a mixture of at least two compounds selected from the group consisting of organic oil, a mineral oil, a siloxane and an organomodified siloxane which comprises the steps of (a) heating the urea derivative solution in a first carrier media above the melting points of said urea derivatives to form a homogeneous solution;

(b) mixing the homogeneous solution of step (a) with a second carrier media having a temperature of less than 25° C., and (c) dispersing the solid particles of the urea derivatives obtained in the carrier medium.

* * * * *